(12) United States Patent
Marsden et al.

(10) Patent No.: US 7,166,090 B2
(45) Date of Patent: Jan. 23, 2007

(54) MEDICINE DROPPER

(75) Inventors: Andrew W. Marsden, Hingham, MA (US); Joseph C. Cacciola, Wrentham, MA (US)

(73) Assignee: Cosco Management, Inc., Wilmington, DE (US)

( * ) Notice: Subject to any disclaimer, the term of this patent is extended or adjusted under 35 U.S.C. 154(b) by 445 days.

(21) Appl. No.: 10/698,680

(22) Filed: Oct. 31, 2003

(65) Prior Publication Data

US 2005/0096610 A1  May 5, 2005

(51) Int. Cl.
*A61M 35/00* (2006.01)

(52) U.S. Cl. ............. 604/290; 604/294; 604/298; 604/310

(58) Field of Classification Search ........ 604/295, 604/310, 294, 298, 316; 222/240; 442/218, 442/216, 207, 188, 187
See application file for complete search history.

(56) References Cited

U.S. PATENT DOCUMENTS

| D109,459 S | 4/1938 | Reynolds |
|---|---|---|
| D184,414 S | 2/1959 | Wilhelmi |
| D187,170 S | 2/1960 | Hill et al. |
| 3,128,920 A | 4/1964 | Volckening et al. |
| 3,133,635 A | 5/1964 | Gordon et al. |
| 3,186,628 A | 6/1965 | Rohde |
| 3,214,142 A | 10/1965 | Brown et al. |
| 3,295,523 A | 1/1967 | Weichselbaum |
| 3,353,664 A | 11/1967 | Armentrout et al. |
| 3,435,944 A | 4/1969 | Ishii |
| D215,169 S | 9/1969 | Stephenson |
| 3,670,730 A | 6/1972 | White |
| D234,228 S | 1/1975 | Spiegel |
| D243,636 S | 3/1977 | Rubin et al. |
| D362,387 S | 9/1995 | Shumer |
| 6,814,265 B1 * | 11/2004 | Clifford et al. ............. 222/420 |

* cited by examiner

*Primary Examiner*—Jacqueline F. Stephens
(74) *Attorney, Agent, or Firm*—Barnes & Thornburg LLP

(57) ABSTRACT

According to the present disclosure, a monolithic medicine dropper, for storing and dispensing liquids, includes a first portion resiliently compressible at one end. Also included is at least a second portion fluidly connected with the first portion and being essentially rigid and hollow and having an opening. At least one of the portions includes written indicia thereon indicating liquid capacities and content levels of the dropper.

19 Claims, 2 Drawing Sheets

MEDICINE DROPPER

BACKGROUND

The present disclosure relates to medicine droppers, and more particularly, to medicine droppers for storing and dispensing liquids.

Droppers or syringes for dispensing liquids are known. Some are one-piece devices having a compressible bulb part and a generally more rigid tubular-like part that holds a liquid to be dispensed. The bottom part may have one or more liquid content-level markings. Such devices may be contained in sealed packages.

SUMMARY

Accordingly to the present disclosure, a medicine dropper, for storing an dispensing liquids, includes a first portion resiliently compressible at a first end and being essentially rigid and hollow between the first end and a second end. Also included is second portion, monolithically constructed and in fluid communication with the first portion. The second portion is essentially rigid and hollow between a third end and a fourth end. Further included is a third portion, monolithically constructed and fluidly connected with the second portion. The third portion is essentially rigid and hollow between a fifth end that tapers to a sixth end having an opening.

The three portions may have identical cross-sections, which may be essentially cylindrical, elliptical or rectangular.

The cross-sections of each portion may be differently dimensioned and form at least one step at a junction between two of the portions.

At least one of the portions may include written indicia thereon, indicating liquid capacities and content levels of the dropper.

Other aspects of the present disclosure will become apparent from the following descriptions when considered in conjunction with the accompanying drawings.

DETAILED DESCRIPTION OF THE DRAWINGS

Figure 1:
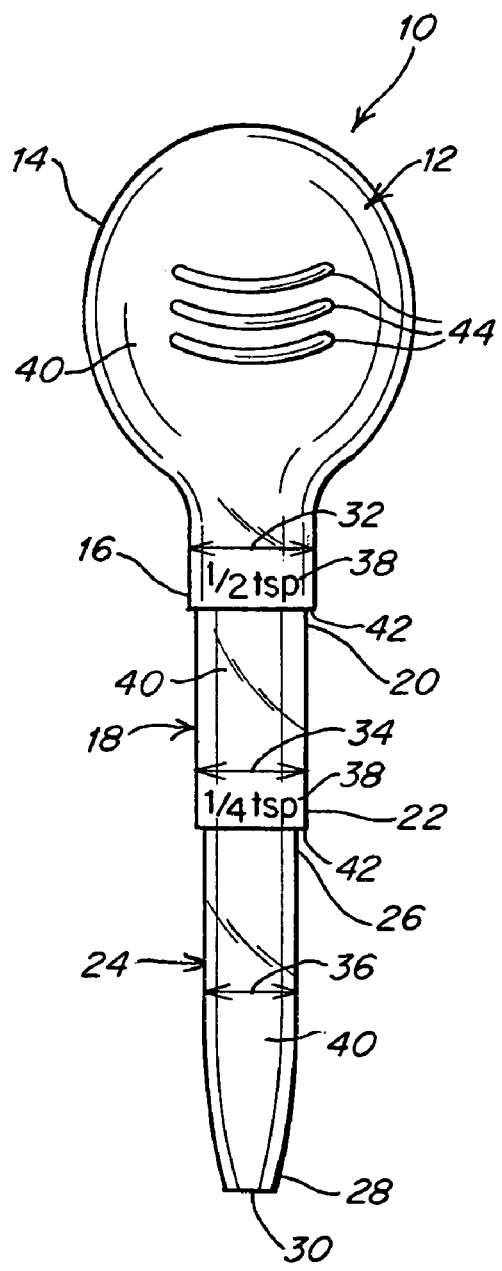
FIG. 1 is an elevational view of an embodiment of a medicine dropper, according to the principles of the present disclosure.

An embodiment of a medicine dropper 10, for storing and dispensing liquids, is shown, for example, in FIG. 1. Dropper 10 includes a first portion 12 that is essentially rigid and that is resiliently compressible at a first end 14. The first portion 12 is hollow between the first end 14 and a second end 16. Also included is a second portion 18, monolithically constructed and in fluid communication with the first portion 12 and being essentially rigid and hollow between a third end 20 and a fourth end 22. Further included is a third portion 24, monolithically constructed and in fluid communication with the second portion 18 and being essentially rigid and hollow between a fifth end 26 that tapers to a sixth end 28 having an opening 30.

At least one of the portions 12, 18, 24 may include written indicia 38 indicating liquid capacities and content levels of the dropper 10. FIG. 1 shows portions 12 and 18 having indicia 38, for example, ¼ tsp and ½ tsp.

Figure 2:
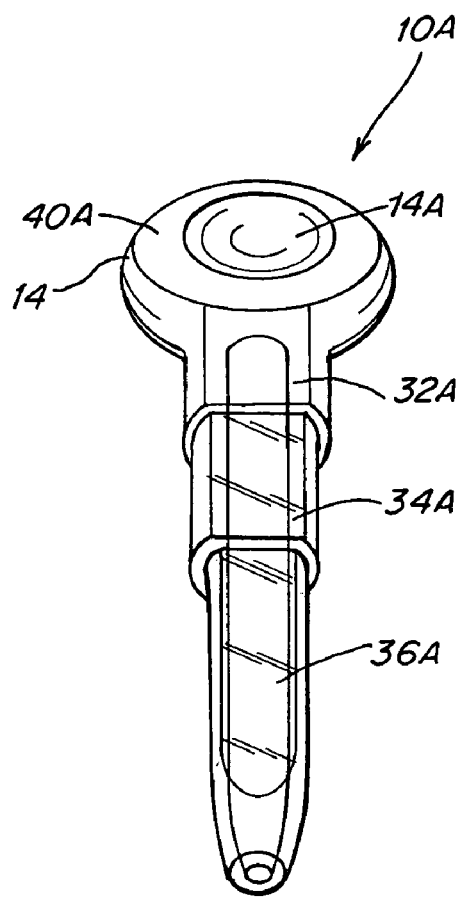
FIG. 2 is a perspective view of another embodiment of a medicine dropper, according to the principles of the present disclosure.

The first portion 12 may have a first cross-section 32. The section portion 18 may have second cross-section 34. The third portion 24 may have a third cross-section 36. The first, second and third cross-sections 32, 34, 36, respectively, may be essentially cylindrical, elliptical or rectangular. In an embodiment of a dropper 10A, as shown in FIG. 2, a portion 32A, 34A, 36A of each cross-section 32, 34, 36 may be planar (see FIG. 2). A surface of the planar portion 32A, 34A, 36A may also include indicia, for example, 1.25 ml and 3.0 ml (not shown). The first end 14 may also include at least one indentation 14A (see FIG. 2) on an opposite outer surface 40A from surface 40. Each of the at least one indentations 14A may be configured such that at least a portion of a user's finger tip could fit into the at least one indentation 14A to assist in a squeezing of the first end 14 when dispensing liquid from the dropper 10. The first, second and third cross-sections 32, 34, 36, respectively, may be differently dimensioned, as shown in FIG. 1, and descending in dimension from the first cross-section 32 to the third cross-section 36. For example, cross-section 32 may be essentially cylindrical, as shown in FIG. 1 and its cross-section dimension may be approximately 1 cm, cross-section 34 may be approximately 0.9 cm and cross-section 36 may be approximately 0.8 cm. Or, one or more of the three cross-sections 32, 34, 36, respectively, may be substantially the same dimensionally (not shown).

The first end 14 may be bulb-shaped, as shown in FIG. 1. Other shapes are conceivable. The portions 12, 18, 24 may have outer surfaces 40 and the written indicia 38 may be on at least one of the outer surfaces 40, as shown in FIG. 1.

In the embodiment shown in FIG. 1, the three different cross-sections 32, 34, 36, respectively, may form steps or shoulders 42 which may provide, among other things, easily observed/detected content levels of the dropper 10 by viewing and/or touching one or more of the shoulders 42. Alternatively, ridges (not shown) may be formed at appropriate indicia points.

The first end 14 may include at least one raised ridge 44 on the outer surface 40 adjacent first end 14. The embodiment in FIG. 1 shows, for example, three raised ridges 40. The raised ridges 40, may, for example, help prevent a user's hand from slipping when squeezing or compressing the first end 14.

The dropper 10 may be made from plastic or equivalent material and one or more portions 12, 18, 24 may be translucent. The dropper 10 may be made monolithically and blow molded or manufactured by other equivalent methods. An enclosing wall thickness of the first end 14 may be less than an enclosing wall thickness of the second end 16 and of the second and third portions 18, 24. In such an embodiment, the first portion 14 will be more easily compressible than the second end 16 and the first and second portions 18, 24, which are sufficiently more rigid so as to essentially resist compression.

Figure 3:
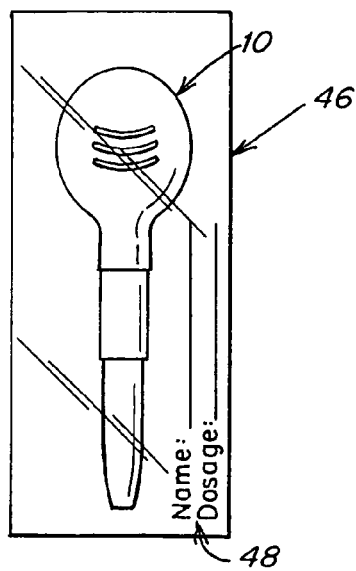
FIG. 3 is an elevational view of the medicine dropper of FIG. 1 in a sealable package. package.
Figure 4:
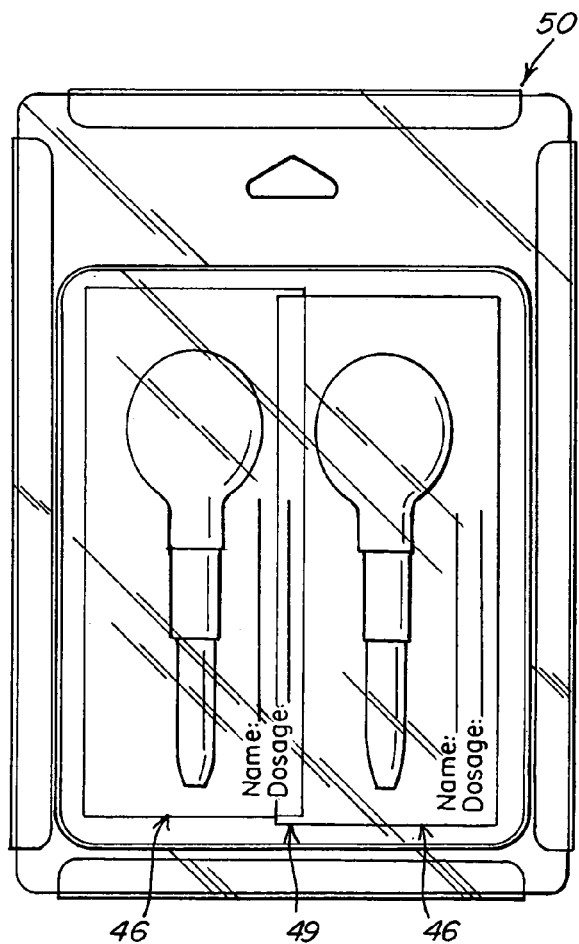
FIG. 4 is a perspective view of a plurality of packaged medicine droppers in a consolidated package, according to the principles of the present disclosure.

The dropper 10 may be disposable or reusable, and one or more droppers 10 may be insertable in a package 46, with package 46 having one dropper 10, as shown in FIG. 3. The package 46 may, for example, be a bag, as shown in FIG. 3, which bag may be sealable and/or reusable. The package 46 may also be, for example, a blister pack (not shown) that may be heat sealed. The package 46 may be markable with, for example, user or patient information such as name and dosage 48, as shown in FIG. 3. As shown in FIG. 4, a plurality 49 (shown, for example, as two) of packaged droppers 46 may in turn be placed in a consolidated package 50 The package 50 is adapted to be releasably enclosed and/or sealed (not shown).

Although the present disclosure has been described and illustrated in detail, it is to be clearly understood that this is done by way of illustration and example only and is not to be taken by way of limitation. The spirit and scope of the present disclosure are to be limited only by the terms of the appended claims.

We claim:

1. A medicine dropper for storing and dispensing liquids, comprising:
    a first portion, being resiliently compressible at a first end and being essentially rigid and hollow between the first end and a second end;
    a second portion being monolithically constructed and in fluid communication with the first portion, the second portion being essentially rigid and hollow between a third end and a fourth end;
    a third portion, monolithically connected and in fluid communication with the second portion, the third portion being essentially rigid and hollow between a fifth end that tapers to a sixth end having an opening; and
    wherein the first end includes an outer wall, and a thickness of the outer wall of the first end is less than a thickness of an outer wall of each of the second end and of the second and third portions.

2. The dropper of claim 1, wherein the first portion has a first cross-section, the second portion has a second cross-section and the third portion has a third cross-section.

3. The dropper of claim 2, wherein the first, second and third portions are essentially cylindrical in cross-section.

4. The dropper of claim 2, wherein the first, second and third portions are essentially elliptical in cross-section.

5. The dropper of claim 2, wherein the first, second and third portions are essentially rectangular in cross-section.

6. The dropper of claim 2, wherein the first, second and third cross-sections are differently-dimensioned and descending in dimension from the first cross-section to the third cross-section.

7. The dropper of claim 6, wherein the differently dimensioned cross-sections form at least one step at a junction between two portions.

8. The dropper of claim 1, wherein at least one of the portions includes written indicia thereon indicating liquid capacities and content levels of the dropper.

9. The dropper of claim 8, wherein the at least one portion includes an outer surface, the outer surface having the written indicia.

10. The dropper of claim 1, wherein the first end is bulb-shaped.

11. The dropper of claim 1, wherein the dropper is constructed monolithically.

12. The dropper of claim 1, wherein the dropper is blow molded.

13. The dropper of claim 1, wherein the first end includes at least one raised ridge on an outer surface.

14. The dropper of claim 1, wherein the first end includes at least one indentation on an outer surface.

15. The dropper of claim 1, wherein at least one of the portions is translucent.

16. The dropper of claim 1, wherein the dropper is disposable.

17. The dropper of claim 1, wherein at least one dropper is inserted and sealed in a package.

18. The dropper of claim 17, wherein the package is a sealable bag.

19. The dropper of claim 17, wherein the at least one dropper sealed in a package is a plurality of droppers sealed in a package and the plurality of droppers sealed in a package are in a consolidated package.

* * * * *